United States Patent
Yanase (10) Patent No.: US 12,171,574 B2
(45) Date of Patent: Dec. 24, 2024

(54) FASTENER

(71) Applicant: icuco Inc., Aichi (JP)

(72) Inventor: Yoichi Yanase, Aichi (JP)

(73) Assignee: ICUCO INC., Aichi (JP)

( * ) Notice: Subject to any disclaimer, the term of this patent is extended or adjusted under 35 U.S.C. 154(b) by 102 days.

(21) Appl. No.: 17/911,048

(22) PCT Filed: Mar. 1, 2021

(86) PCT No.: PCT/JP2021/007644
§ 371 (c)(1),
(2) Date: Sep. 12, 2022

(87) PCT Pub. No.: WO2021/187067
PCT Pub. Date: Sep. 23, 2021

(65) Prior Publication Data
US 2023/0109091 A1 Apr. 6, 2023

(30) Foreign Application Priority Data

Mar. 16, 2020 (JP) ................................ 2020-045056

(51) Int. Cl.
*A61B 5/11* (2006.01)
*A61B 5/00* (2006.01)

(52) U.S. Cl.
CPC ............. *A61B 5/6802* (2013.01); *A61B 5/11* (2013.01); *A61B 2562/02* (2013.01)

(58) Field of Classification Search
CPC ..... A61B 5/6802; A61B 5/11; A61B 2562/02; A44B 99/00; G01P 15/18
See application file for complete search history.

(56) References Cited

U.S. PATENT DOCUMENTS 3,745,616 A * 7/1973 Batts .................... A47G 25/485
24/562
4,805,633 A * 2/1989 Kotani .................... A61B 7/04
600/528

(Continued)

FOREIGN PATENT DOCUMENTS

| JP | 3141422 U | 4/2008 |
| JP | 2014-502188 A | 1/2014 |

(Continued)

OTHER PUBLICATIONS

Written Opinion issued in International Bureau of WIPO Patent Application No. PCT/JP2021/007644, dated Apr. 27, 2021, along with an English translation thereof.

(Continued)

*Primary Examiner* — David M Upchurch
(74) *Attorney, Agent, or Firm* — Greenblum & Bernstein, P.L.C.

(57) ABSTRACT

A fastener according to the present disclosure includes a main unit, an adjuster unit which extends from the main unit and which is capable of being elastically inflected, and a cover unit coupled to the main unit through the adjuster unit. The cover unit is configured to be, by elastic flection of the adjuster unit, both in a state apart from the main unit and in a state latched with the main unit so as to cover the main unit, and with the cover unit being in the state latched with the main unit, a side surface of the main unit and a surface of the adjuster unit are apart from each other, the surface of the adjuster unit facing the side surface.

6 Claims, 9 Drawing Sheets

(56) References Cited

U.S. PATENT DOCUMENTS

| | | | | |
|---|---|---|---|---|
| 4,825,516 | A * | 5/1989 | Ackermann | B29C 66/1352 24/465 |
| 5,160,339 | A * | 11/1992 | Chen | A61B 17/1285 606/157 |
| 6,311,935 | B1 * | 11/2001 | Mullen, Jr. | H02G 3/32 248/74.1 |
| 6,514,027 | B1 * | 2/2003 | Yiu | E05B 79/12 411/433 |
| 7,881,762 | B2 * | 2/2011 | Kling | A61B 5/6838 600/323 |
| 8,157,222 | B1 * | 4/2012 | Shirey | H02G 3/32 248/68.1 |
| 8,417,309 | B2 * | 4/2013 | Price | A61B 5/6826 600/323 |
| 8,515,512 | B2 * | 8/2013 | Ollerdessen | A61B 5/6838 600/323 |
| 9,220,507 | B1 * | 12/2015 | Patel | A61B 17/064 |
| 10,993,660 | B2 * | 5/2021 | Palley | A61B 5/14551 |
| 2001/0054671 | A1 * | 12/2001 | Kondo | F16L 3/1025 248/68.1 |
| 2005/0075550 | A1 * | 4/2005 | Lindekugel | A61B 5/14552 600/344 |
| 2005/0285375 | A1 * | 12/2005 | Kawai | B60R 21/215 280/730.2 |
| 2008/0076996 | A1 * | 3/2008 | Hoarau | A61B 5/7207 600/323 |
| 2010/0096570 | A1 * | 4/2010 | Kashmirian | A61M 39/284 251/9 |
| 2013/0018364 | A1 * | 1/2013 | Chernov | A61B 18/1442 606/49 |
| 2013/0110264 | A1 * | 5/2013 | Weast | H04B 1/385 700/91 |
| 2013/0310636 | A1 | 11/2013 | Krans et al. | |
| 2014/0060655 | A1 * | 3/2014 | Ramos | F16K 7/063 251/9 |
| 2015/0156109 | A1 * | 6/2015 | Skaaksrud | H04W 4/02 709/239 |
| 2015/0380141 | A1 | 12/2015 | Mayfield | |
| 2016/0015289 | A1 * | 1/2016 | Simon | A61B 5/4041 600/301 |
| 2016/0051793 | A1 * | 2/2016 | Gibson-Horn | A61B 5/16 600/26 |
| 2016/0091866 | A1 * | 3/2016 | Jersa, III | B42F 1/006 368/278 |
| 2016/0317089 | A1 * | 11/2016 | Fyfe | A61B 5/0002 |
| 2017/0112398 | A1 | 4/2017 | Narusawa | |
| 2017/0172222 | A1 * | 6/2017 | Morgenthau | G01P 15/0891 |
| 2017/0312427 | A1 * | 11/2017 | Steger | F16K 7/045 |
| 2018/0015894 | A1 * | 1/2018 | Zaldivar Ortiz | B60R 16/0215 |
| 2019/0374122 | A1 * | 12/2019 | Kuenzi | A61B 5/6831 |
| 2021/0030420 | A1 * | 2/2021 | Pilletere | A61B 17/122 |
| 2021/0100503 | A1 * | 4/2021 | Olwal | A61B 5/683 |
| 2022/0264964 | A1 * | 8/2022 | Matsuoka | G01K 1/14 |

FOREIGN PATENT DOCUMENTS

| | | |
|---|---|---|
| JP | 2014-129104 A | 7/2014 |
| JP | 2015-188498 A | 11/2015 |
| JP | 2016-67811 A | 5/2016 |
| JP | 2016-152859 A | 8/2016 |
| JP | 2017-149452 A | 8/2017 |
| JP | 2017-164537 A | 9/2017 |
| JP | 2019-123557 A | 7/2019 |
| JP | 2020-25299 A | 2/2020 |
| WO | 2012/069962 A1 | 5/2012 |
| WO | 2014/071186 A1 | 5/2014 |
| WO | 2015/146138 A1 | 10/2015 |

OTHER PUBLICATIONS

International Search Report issued in International Bureau of WIPO Patent Application No. PCT/JP2021/007644, dated Apr. 27, 2021, along with an English translation thereof.

* cited by examiner

FASTENER

TECHNICAL FIELD

The present disclosure relates to a structure of a fastener.

BACKGROUND ART

Regarding a sensor attached to a body, technologies disclosed in the following patent documents are example background arts.

Patent Document 1 discloses a biological information detecting device that detects biological information including a pulse wave of a user, etc., by causing a band portion to which a sensor portion is attached to be wrapped around the wrist of the user.

Moreover, Patent Document 2 discloses a biological information detecting device of which a base portion including a pulse wave sensor is attached to the wrist of a user by a holding mechanism like a band. The biological information detecting device detects the attachment and detachment of itself based on a detection signal from the pulse wave sensor.

CITATION LIST

Patent Literatures

Patent Document 1: JP 2015-188498 A
Patent Document 2: JP 2017-164537 A

SUMMARY OF INVENTION

Technical Problem

The care of an infant is a large burden for a childminder, a babysitter, or parents.

For example, it is difficult for such a person to look aside even if an infant is taking a nap, etc. This makes the work burden for a childminder, etc., or the childcare burden for parents quite large.

In recent years, as a scheme for reducing such burdens, it is attempted to attach a body motion sensor to an infant so as to enable detection of abnormalities in the infant, such as the abnormality in pulse, the abnormality in body temperature and a state in which there is no body motion. In this case, the body motion sensor outputs an alert when detecting the abnormality in the infant, so that a childminder, etc., can be aware of such abnormality. This spares the need for the childminder, etc., to always stay around the infant.

However, an alert may be output when the body motion sensor is not attached properly, or when the attachment state of the body motion sensor becomes not suitable for detection because of the motion, etc., of the infant.

In this case, although the infant is in a normal condition, it is necessary for the childminder, etc., to immediately run up to the infant and to check the condition thereof. In particular, displacement of the attached body motion sensor often occurs due to the roll-over of the infant while taking a nap, and to the activity during playing. This increases the output frequency of the alert, unintendedly increasing the work burdens in some cases.

Accordingly, in view of such technical problems, an objective of the present disclosure is to provide a structure of a fastener that is suitable for the attachment of a body motion sensor.

Solution to Problem

A fastener according to the present disclosure includes:
a main unit;
an adjuster unit which extends from the main unit and which is capable of being elastically inflected; and
a cover unit coupled to the main unit through the adjuster unit,
in which the cover unit is configured to be, by elastic flection of the adjuster unit, both in a state apart from the main unit and in a state latched with the main unit so as to cover the main unit, and
in which with the cover unit being in the state latched with the main unit, a side surface of the main unit and a surface of the adjuster unit are apart from each other, the surface of the adjuster unit facing the side surface.

Accordingly, in the state in which the cover unit is latched with the main unit, the inflected adjuster unit produces slight leeway for positioning of the cover unit in the latching direction.

According to the above-described fastener, the cover unit may be latched with the main unit so as to cover equal to or smaller than a half of the main unit.

Hence, in the state in which the cover unit is latched with the main unit, a part of the main unit is exposed to the exterior.

According to the above-described fastener, the main unit may include a protrusion, the cover unit may be provided with an insertion opening, and the protrusion may be fitted in the insertion opening in the state in which the cover unit is latched with the main unit.

When the cover unit is removed from the main unit, an unlatched state can be easily accomplished by lifting up the cover unit from the main unit so as to peel with the exposed protrusion being depressed.

According to the above-described fastener, a body motion sensor that includes one or a plurality of detecting units capable of detecting a body situation of a wearing person may be attached to the main unit.

Hence, in the state in which the fastener is attached to the fabric of the clothing of the wearing person by latching the cover unit with the main unit, the body motion sensor contacts the body of the wearing person.

According to the above-described fastener, the detecting unit may include at least an optical sensor to determine a contact state with a body of the wearing person, and the optical sensor may be placed so as to be exposed from an opening formed in the main unit.

Accordingly, the attachment state of the fastener can be determined using the optical sensor.

Advantageous Effects of Invention

According to the present disclosure, by the structure of the fastener applicable to the body motion sensor, the attachment is facilitated but the detachment is suppressed, such a structure can cope with the thickness of clothing, and the occurrence of an attachment displacement is suppressed.

DESCRIPTION OF EMBODIMENTS

An embodiment will be described below with reference to FIG. 1 to FIG. 15.

Note that a structure illustrated in the figure to be referred in order to describe the embodiment indicates major necessary components and the peripheral structure thereof extracted to carry out the embodiment. Moreover, the figures are merely examples, and the thickness, the relation with a planar dimension, the ratio, etc., of each component illustrated in the figure are merely examples. Hence, various changes can be made in accordance with a system design, etc., without departing from the scope and spirit of the present disclosure.

Moreover, a fastener according to this embodiment is formed in a substantially elliptic cylindrical shape as an example, and in the following description, the external surfaces of a main unit that forms the fastener will be defined as a plane surface (upper surface), a bottom surface (lower surface), side surfaces (both right and left surfaces), a front surface (anterior surface) and a back surface (rear surface), respectively, and those will be references indicating front, back, up, down, right and left directions. Moreover, a direction that connects a plane-surface side (upper-surface side) where the plane surface (upper surface) is present and a bottom-surface side (lower-surface side) where the bottom surface (lower surface) is present will be defined as a vertical direction, a direction that connects a right-surface side where the right surface is present and a left-surface side where the left surface is present will be defined as a horizontal direction, and a direction that connects a front-surface side (anterior-surface side) where the front surface (anterior surface) is present and a back-surface side (rear-surface side) where the back surface (rear surface) is present will be defined as a back-and-forth direction.

1. Outline of Fastener

An outline of a fastener 1 according to this embodiment will be described with reference to FIG. 1 to FIG. 3.

Figure 1:
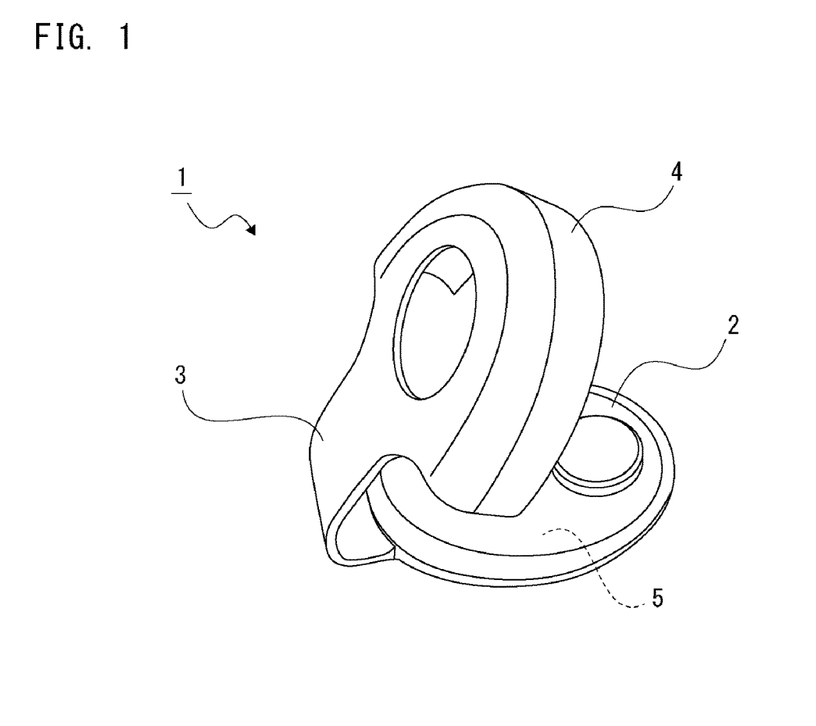
FIG. 1 is a perspective view of a fastener according to an embodiment of the present disclosure.
Figure 2:
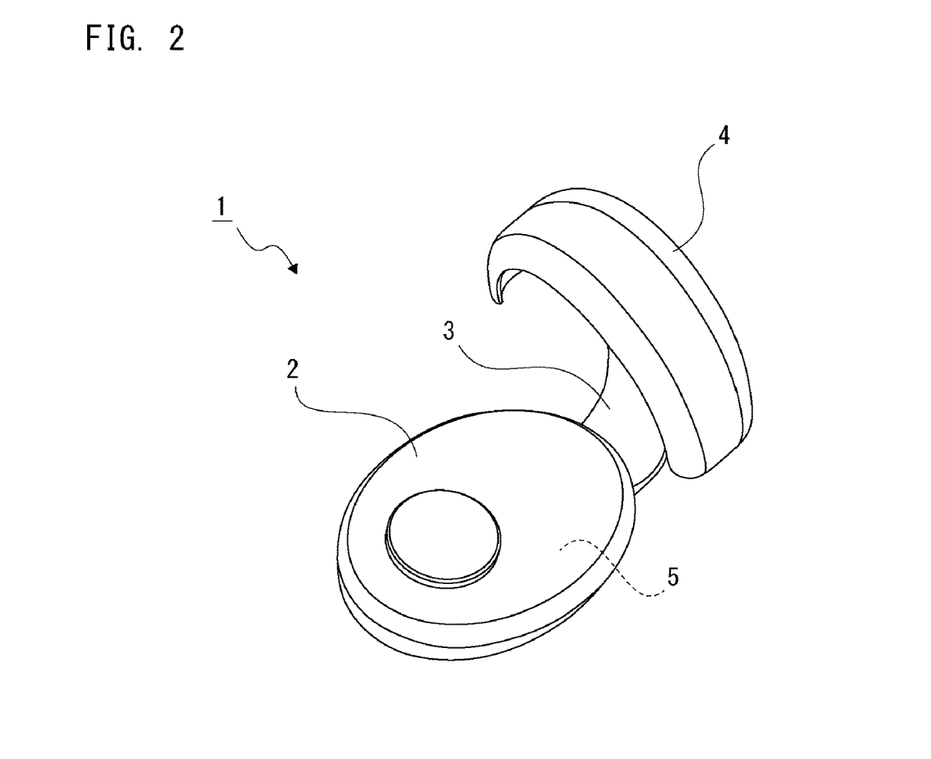
FIG. 2 is a perspective view of the fastener according to the embodiment.
Figure 3:
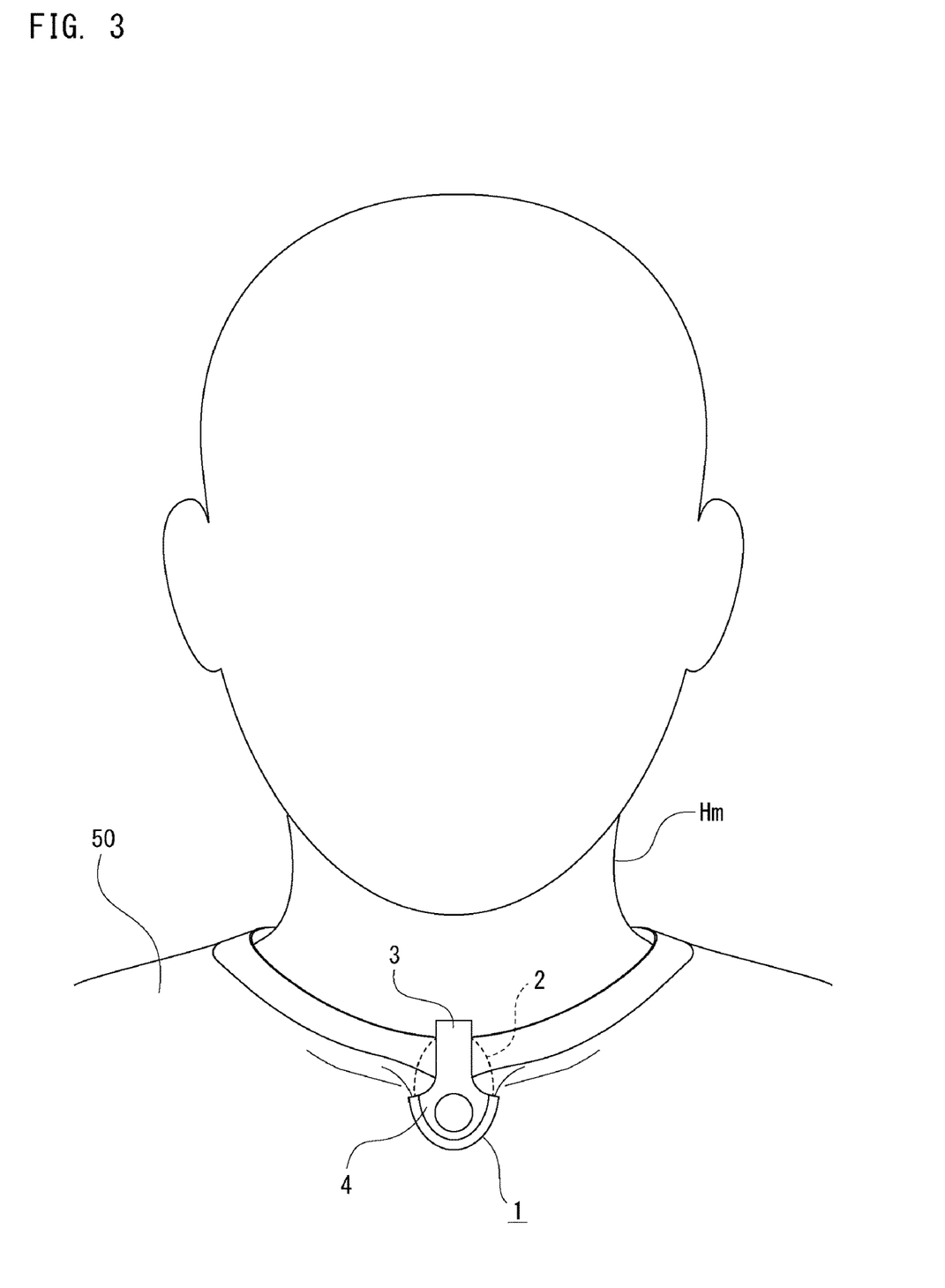
FIG. 3 is a diagram illustrating an attachment state of the fastener according to the embodiment.

FIG. 1 and FIG. 2 are each a perspective view of the fastener 1, and FIG. 3 is a diagram illustrating an attachment state of the fastener 1.

As illustrated in FIG. 1 and FIG. 2, the fastener 1 according to this embodiment includes the main unit 2 in which a body motion sensor 5 is built, an adjuster unit 3 extending from the main unit 2, and a cover unit 4 coupled to the main unit 2 through the adjuster unit 3.

As illustrated in, for example, FIG. 3, the fastener 1 is to be attached to the clothing of an infant Hm by causing the cover unit 4 to be latched with the main unit 2 so as to pinch the fabric 50 of the clothing of the infant Hm therebetween.

By attaching the fastener 1 to the clothing of the infant Hm, the body situation of the infant Hm can be sensed by the body motion sensor 5 retained in the main unit 2.

As for the other schemes of fastening a device like the body motion sensor 5, etc., to the clothing, for example, a clip scheme that utilizes a plate spring, and a button scheme that utilizes the elasticity of a resin are considerable. According to those schemes, however, there is a tendency such that the number of components increases, and thus the production costs increase. Moreover, according to the button scheme, the components are divided into equal to or greater than two components, and thus there is a possibility such that any component may be lost, and the capability to be attached to the thick clothing is low.

Accordingly, by integrating a button-type cover with a casing, the structure of the fastener 1 provided with the adjuster unit 3 which is illustrated in FIG. 1 and FIG. 2, can reduce the production cost and the number of components, and can be attached to thick clothing is proposed.

2. Structure of Fastener

Next, the structure of the fastener 1 will be described with reference to FIG. 4 to FIG. 14.

FIG. 4 to FIG. 8 respectively illustrate a plan view (FIG. 4), a bottom view (FIG. 5), a front view (FIG. 6), a back view (FIG. 7) and a right side view (FIG. 8) of the fastener 1 in a state in which the latching of the main unit 2 is released and the cover unit 4 is opened (also referred to as an unlatched state below). Note that regarding the left side view, since it is substantially the same structure as that of the right side view, the illustration will be omitted.

Moreover, FIG. 9 to FIG. 14 respectively illustrate a plan view (FIG. 9), a bottom view (FIG. 10), a front view (FIG. 11), a back view (FIG. 12), a right side view (FIG. 13) and a cross-sectional view (FIG. 14) taken along a line A-A in FIG. 9 of the fastener 1 in a state in which the cover unit 4 is latched with the main unit 2 (also referred to as a latched state below). Regarding the left side view, also, since it is substantially the same structure as that of the right side view, the illustration will be omitted.

As described above, the fastener 1 illustrated in FIG. 4 to FIG. 14 includes the main unit 2, the adjuster unit 3 and the cover unit 4. These components are formed of, for example, a resin, such as polyethylene (PE) or polypropylene (PP).

The main unit 2 includes a casing lid 21 and a storage casing 22. The main unit 2 is formed by coupling the casing lid 21 and the storage casing 22 with each other up and down.

The casing lid 21 is formed in a substantially elliptic cylindrical shape that is opened downwardly. A cylindrical protrusion 24 is formed on an upper surface 23 of the casing lid 21. The cylindrical protrusion 24 is fitted in a circular opening 45 formed in the cover unit 4 to be described later in a latched state.

The storage casing 22 is formed in a substantially elliptic cylindrical shape that is opened upwardly. A plurality of and a predetermined number of bottom-surface openings 26 is formed in a bottom surface 25 of the storage casing 22. A sensing surface, etc. of the body motion sensor 5 to be described later is placed in the bottom-surface opening 26.

Figure 5:
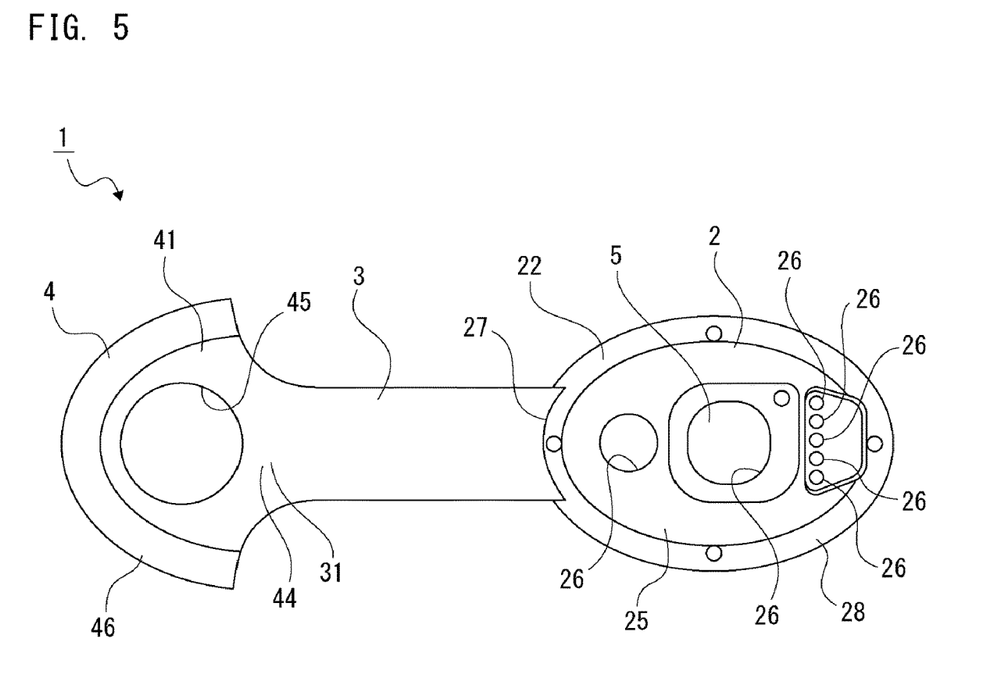
FIG. 5 is a bottom view of the fastener in the unlatched state according to the embodiment.
Figure 6:
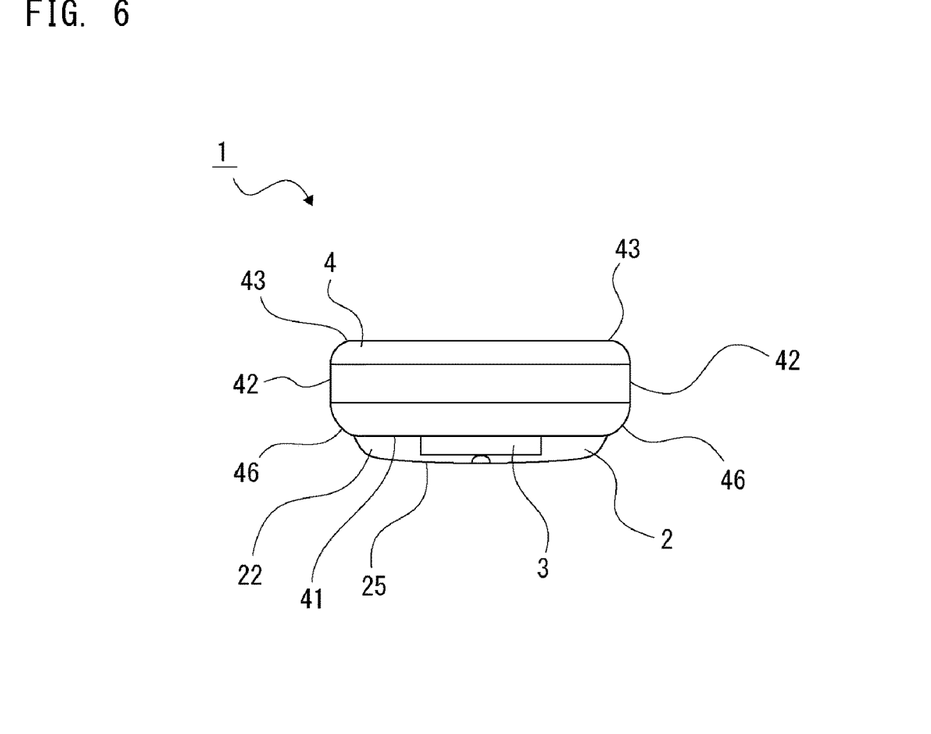
FIG. 6 is a front view of the fastener in the unlatched state according to the embodiment.
Figure 7:
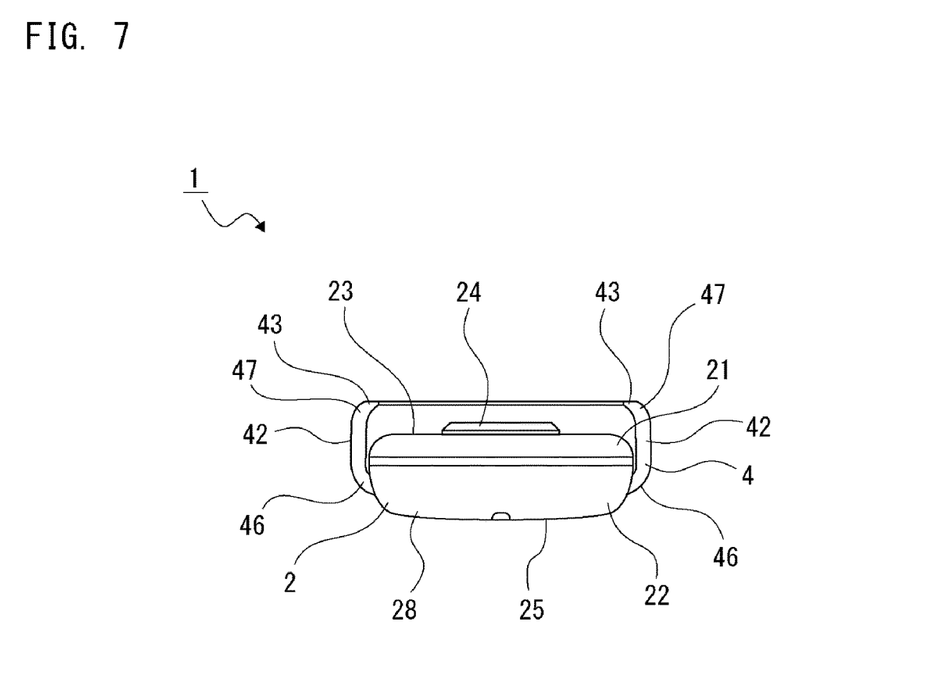
FIG. 7 is a back view of the fastener in the unlatched state according to the embodiment.
Figure 10:
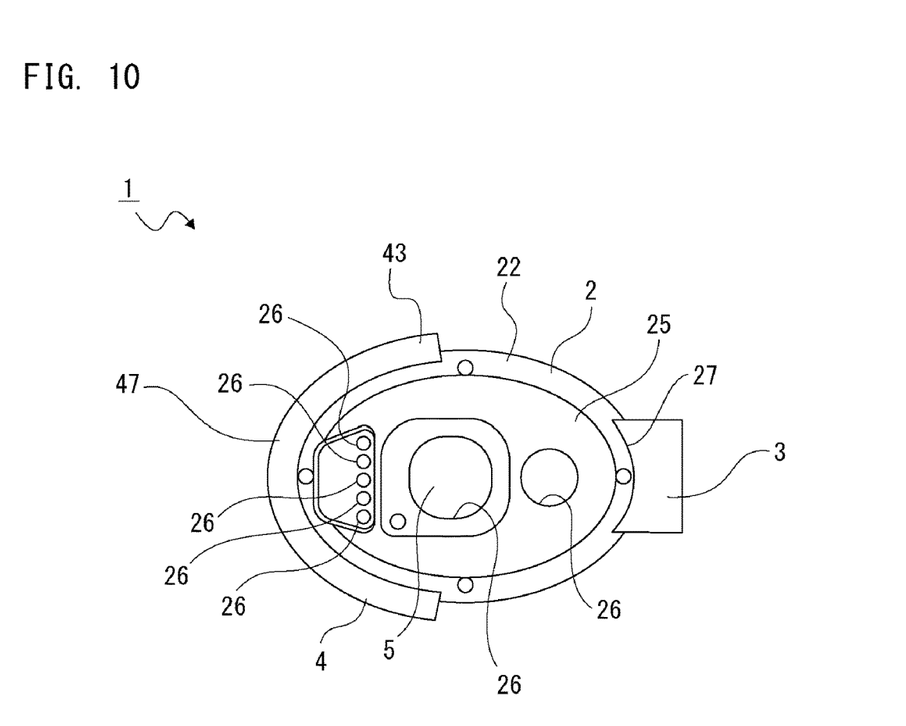
FIG. 10 is a bottom view of the fastener in the latched state according to the embodiment.
Figure 14:
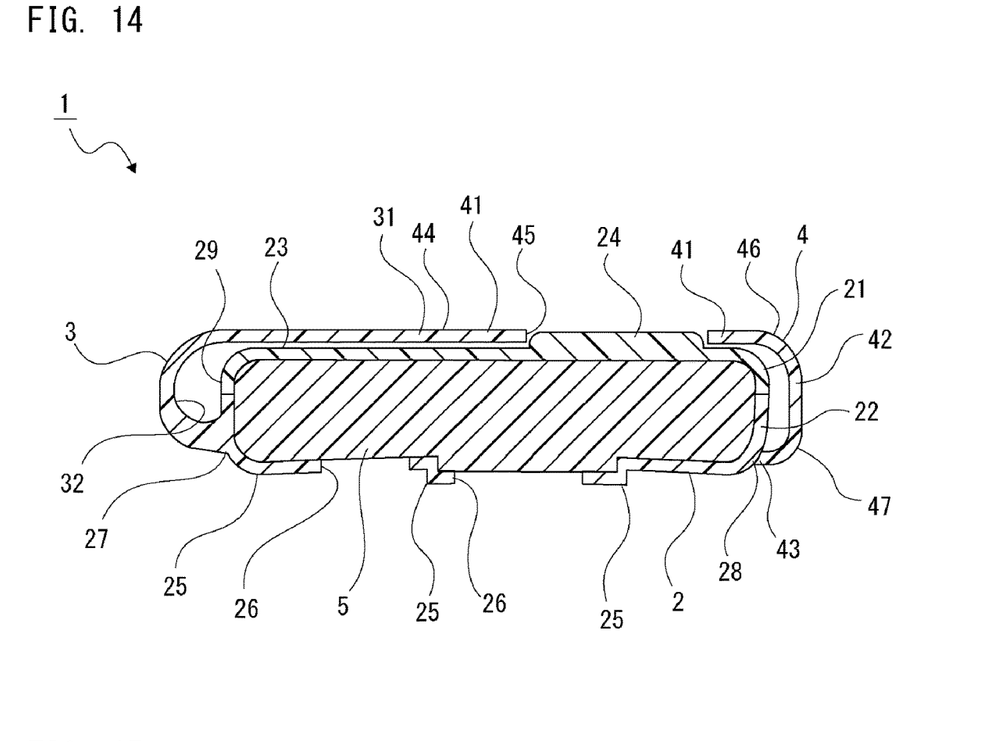
FIG. 14 is an A-A cross-sectional view of the fastener in the latched state according to the embodiment.

As illustrated in FIG. 5, FIG. 10 and FIG. 14, the body motion sensor 5 is attached to an internal space formed in the main unit 2.

The body motion sensor 5 includes one or a plurality of detecting units. The body motion sensor 5 has the built-in detecting unit that is a sensor, such as an optical sensor, a triaxial accelerometer, or a temperature sensor, and has a back surface that is the sensing surface. This sensing surface is placed in the bottom-surface opening 26 of the storage casing 22, thus being exposed to the exterior of the main unit 2.

When the fastener 1 is attached to the clothing of the infant Hm as illustrated in FIG. 3, the sensing surface exposed from the bottom-surface openings 26 of the main unit 2 can contact the skin of the infant Hm, and thus a pulse, a body motion and a body temperature can be sensed. The body motion sensor 5 detects an abnormality in the infant from each piece of sensing information.

Moreover, the body motion sensor 5 can determine a distance from the sensing surface to the skin of the infant Hm based on the light receiving intensity of an optical sensor that measures a pulse, etc. For example, the body motion sensor 5 determines that a distance from the body motion sensor 5 to the infant Hm is far (the fastener 1 is detached from the clothing of the infant Hm) when the light receiving intensity is low.

The body motion sensor 5 outputs an alert when detecting an abnormality in the infant Hm, and when detecting that the fastener 1 is detached from the clothing of the infant Hm, gives a notification to that effect.

Note that also placed in the bottom-surface openings 26 are a push switch for power ON and OFF of the body motion sensor 5, a full color LED that is a component of the body motion sensor 5, and a charging terminal, etc.

Subsequent to the main unit 2, the adjuster unit 3 will be described.

Figure 8:
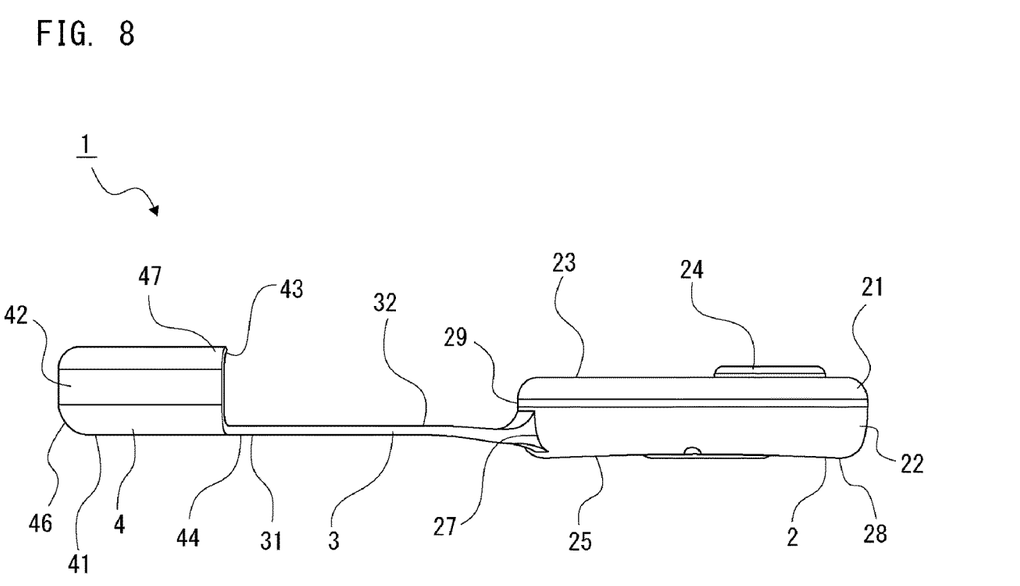
FIG. 8 is a right side view of the fastener in the unlatched state according to the embodiment.

The adjuster unit 3 can be elastically inflected, and as illustrated in FIG. 5 and FIG. 8, is formed in a plate shape that extends in the back-and-forth direction from a front end 27 of the storage casing 22, and a leading end 31 of the adjuster unit 3 is coupled to a rear end 44 of the cover unit 4.

Figure 11:
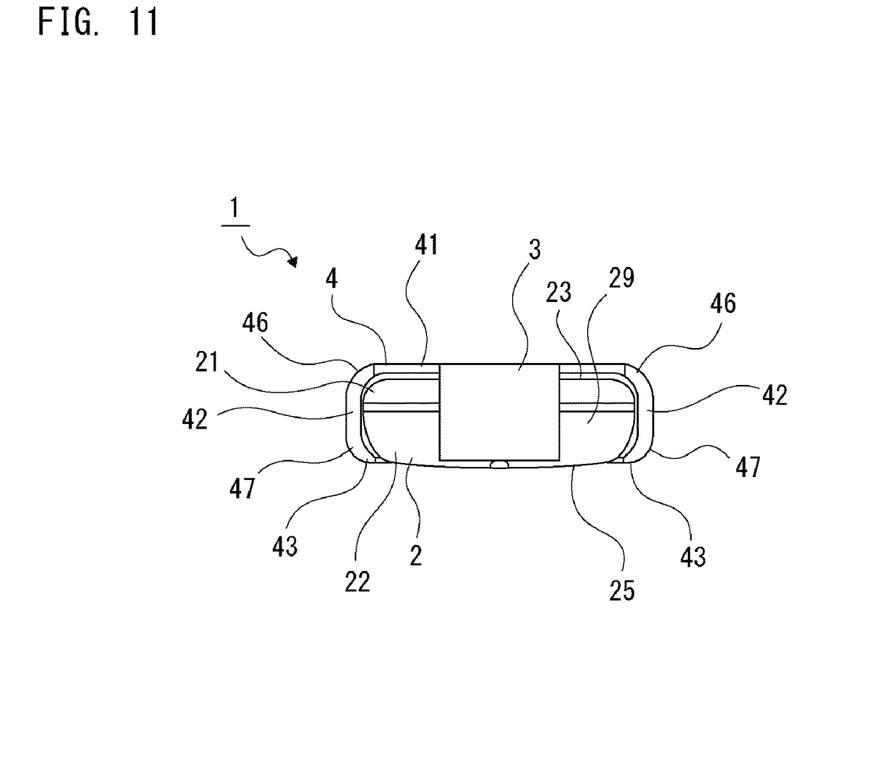
FIG. 11 is a front view of the fastener in the latched state according to the embodiment.
Figure 12:
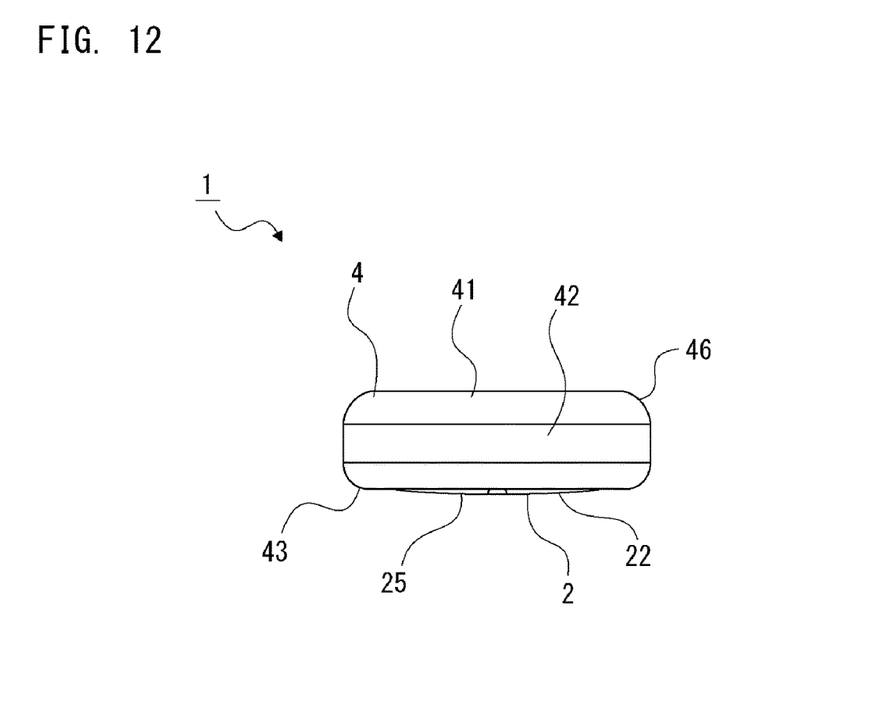
FIG. 12 is a back view of the fastener in the latched state according to the embodiment.
Figure 13:
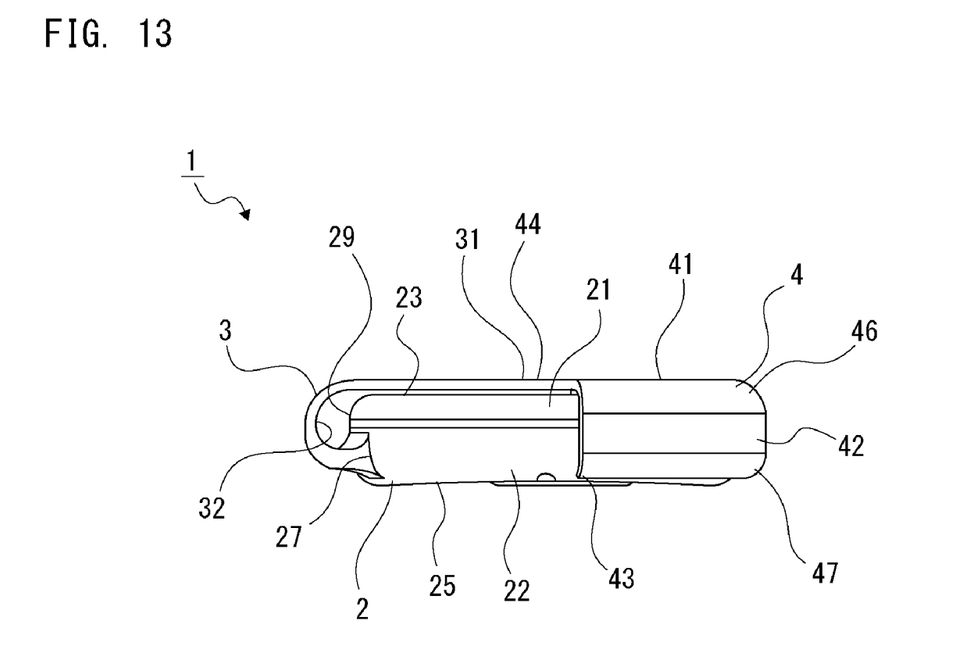
FIG. 13 is a right side view of the fastener in the latched state according to the embodiment.

As illustrated in FIG. 11, FIG. 13 and FIG. 14, the cover unit 4 includes a flat-surface portion 41, a side-surface portion 42, and a latching portion 43.

Figure 9:
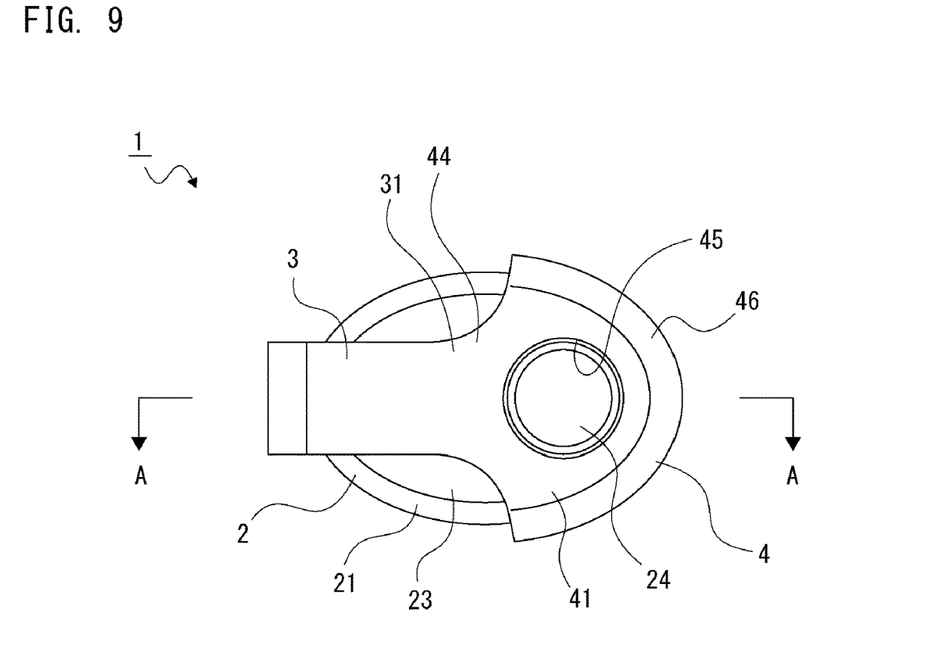
FIG. 9 is a plan view of the fastener in a latched state according to the embodiment.

The flat-surface portion 41 is formed in a substantially semi-elliptical shape so as to cover a part of the upper surface 23 of the main unit 2 illustrated in FIG. 9, e.g., equal to or smaller than the half part. The circular opening 45 is formed in the flat-surface portion 41. In the latched state, the cylindrical protrusion 24 of the main unit 2 is fitted in the circular opening 45.

The side-surface portion 42 protrudes in the thickness direction from a circumferential end edge portion 46 of the flat-surface portion 41, and as illustrated in FIG. 13 and FIG. 14, is formed so as to cover the rear end of the main unit 2 in the latched state.

The latching portion 43 is formed so as to protrude toward the internal side of the radial direction from a lower end edge 47 of the side-surface portion 42.

When the cover unit 4 is caused to be latched with the main unit 2 (caused to be in the latched state), the cover unit 4 is laid over on the main unit 2 by inflecting the adjuster unit 3 in such a way that the latching portion 43 of the cover unit 4 contacts a circumferential end 28 of the bottom surface of the main unit 2. Accordingly, the rear end of the main unit 2 is stored in a storage space defined by the flat-surface portion 41, the side-surface portion 42, and the latching portion 43.

At this time, the cover unit 4 is latched with the main unit 2 since the latching portion 43 of the cover unit 4 is depressed against the main unit 2 by the flection reaction force of the adjuster unit 3.

In such a latched state, a side surface 29 of the main unit 2 and an opposing surface 32 of the adjuster unit 3 facing the side surface 29 are apart from each other.

That is, the cover unit 4 is latched by the main unit 2 in a state covering the main unit 2, but a slight degree of freedom for positioning of the cover unit 4 in the latching direction is given by the adjuster unit 3 in a neck-like shape.

Accordingly, even if the thickness of the fabric 50 of the clothing to be pinched differs, appropriate latching force is obtainable in a pinched state.

Moreover, in the latched state, as illustrated in FIG. 9, FIG. 13 and FIG. 14, the cylindrical protrusion 24 of the main unit 2 is being fitted in the circular opening 45 of the cover unit 4. At this time, the upper surface of the cylindrical protrusion 24 and the upper surface of the cover unit 4 are substantially leveled. The upper surface of the cylindrical protrusion 24 is exposed in this state.

When the cover unit 4 is removed from the main unit 2, a user can easily obtain an unlatched state by lifting up the cover unit 4 from the main unit 2 so as to peel it therefrom with a thumb, etc., being in contact with the cylindrical protrusion 24.

Figure 15:
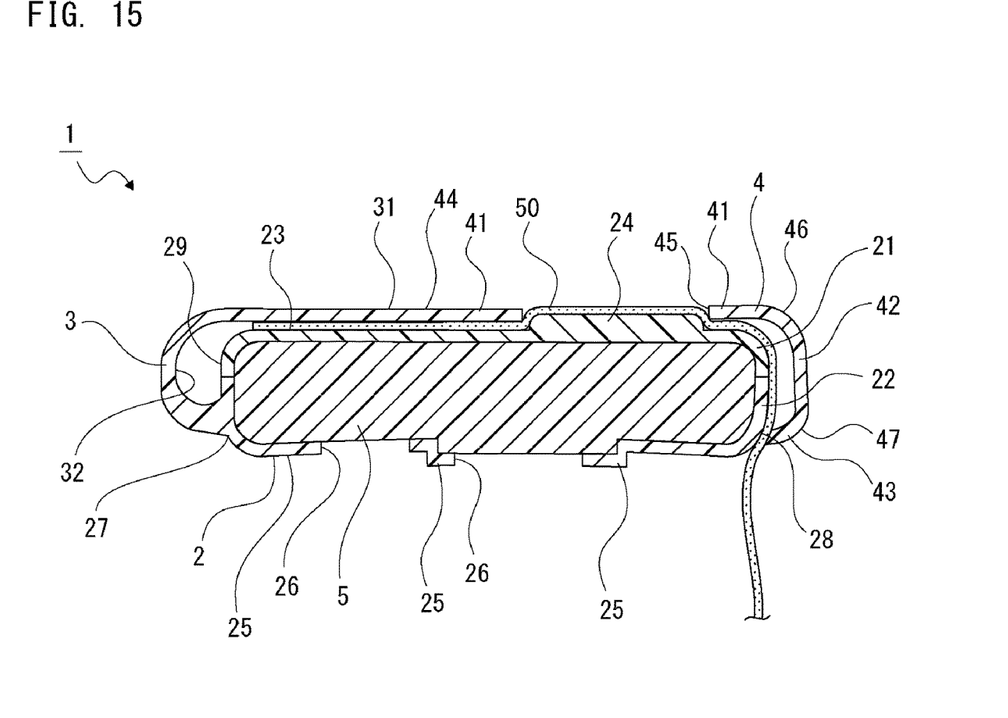
FIG. 15 is an A-A cross-sectional view of the fastener in the latched state according to the embodiment.

A state in which the fastener 1 that employs the above-described structure is attached to the clothing is illustrated in FIG. 3 and FIG. 15.

FIG. 15 is a cross-sectional view taken along a line A-A in FIG. 9 illustrating a state in which the fabric 50 of the clothing is pinched between the main unit 2 and the cover unit 4.

In the unlatched state, for example, the main unit 2 is placed in the clothing of the infant Hm as illustrated in FIG. 3. And the cover unit 4 is laid over thereon so as to pinch the fabric 50 of the clothing, and thus the fastener 1 is attached to the clothing.

In such a latched state, as illustrated in FIG. 15, since the fabric 50 of the clothing is pinched between the main unit 2 and the cover unit 4, the main unit 2 is attached to the fabric 50.

3. Summary and Modified Examples

The fastener 1 according to the above-described embodiment includes the main unit 2, the adjuster unit 3 which extends from the main unit 2 and which is capable of being elastically inflected, and the cover unit 4 coupled to the main unit 2 through the adjuster unit 3 (see, for example, FIG. 1 and FIG. 2).

Figure 4:
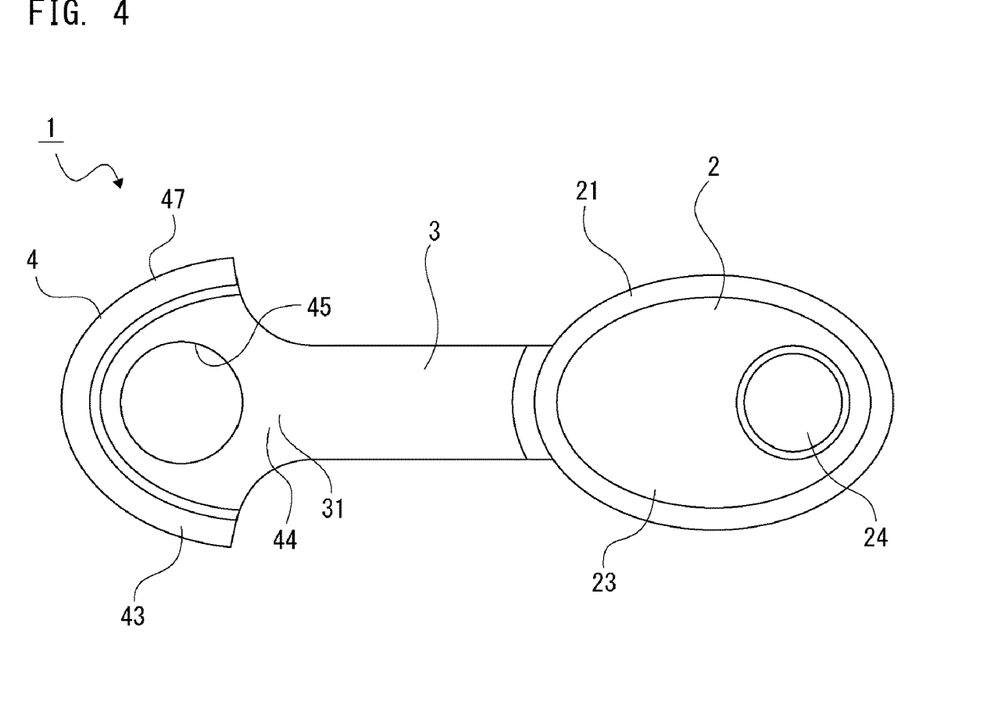
FIG. 4 is a plan view of the fastener in an unlatched state according to the embodiment.

Moreover, the cover unit 4 is configured to be, by elastic flection of the adjuster unit 3, both in a state apart from the main unit 2 and in a state latched with the main unit 2 so as to cover the main unit 2 (see, for example, FIG. 4 and FIG. 9).

With the cover unit 4 being in the state latched with the main unit 2 (the latched state), the side surface 29 of the main unit 2 and the surface 32 of the adjuster unit 3 are apart from each other, the surface of the adjuster unit facing the side surface 29 (see, for example, FIG. 13).

According to the above-described structure, in the latched state, slight leeway for positioning of the cover unit 4 in the latching direction is produced by the adjuster unit 3 in a neck-like shape.

Hence, since appropriate latching force can be obtained in the pinching state even if the thickness of the fabric 50 of the clothing to be pinched between the main unit 2 and the cover unit 4 differs, the attachment displacement of the fastener 1 can be suppressed.

Moreover, even if a component (e.g., the body motion sensor 5) itself to be fastened by the fastener 1 is small, a size that can suppress accidental ingestion of the infant Hm can be easily accomplished by integrating the main unit 2 and the cover unit 4 to each other.

According to the fastener 1 of this embodiment, the cover unit 4 is latched with the main unit 2 so as to cover a part of the main unit 2 (see, for example, FIG. 9 and FIG. 13).

Hence, equal to or greater than the half of the main unit 2 is exposed to the exterior even in the latched state. This improves the heat dissipation efficiency of the body motion sensor 5 attached to the main unit 2.

Moreover, by forming the cover unit 4 so as to cover not the entire main unit 2 but a part thereof, reduction of the production costs of the fastener 1 can be accomplished.

According to the fastener 1 of this embodiment, the main unit 2 includes the protrusion (the cylindrical protrusion 24), the cover unit 4 is provided with the insertion opening (the circular opening 45), and the cylindrical protrusion 24 is fitted in the circular opening 45 in the state in which the cover unit 4 is latched with the main unit 2 (see, for example, FIG. 9 and FIG. 14). When the cover unit 4 is to be removed from the main unit 2, the unlatched state can be easily accomplished by lifting the cover unit 4 from the main unit 2 so as to be peeled therefrom with, for example, the cylindrical protrusion 24 being depressed.

According to the fastener 1 of this embodiment, the body motion sensor 5 that includes one or the plurality of detecting units capable of detecting the body situation of the wearing person (the infant Hm) is attached to the main unit 2 (see, for example, FIG. 14).

Hence, in the state in which the fastener 1 is attached to the fabric 50 of the clothing of the infant Hm by latching the cover unit 4 with the main unit 2, the body motion sensor contacts the body of the infant Hm. Accordingly, the body motion sensor 5 can be easily attached to the clothing of the infant Hm by the fastener 1, and the user, such as a childminder, a babysitter, or parents, can easily monitor the body situation of the infant Hm.

Furthermore, the detecting unit includes at least an optical sensor to determine the contact state with the body of the wearing person (the infant Hm), and the optical sensor is placed so as to be exposed from the opening (the bottom-surface opening 26) formed in the main unit 2 (see, for example, FIG. 5 and FIG. 10).

Accordingly, the attachment state of the fastener 1 can be determined using the optical sensor.

Note that according to this embodiment, although the component attached to the main unit 2 is the body motion sensor 5, such a component is not limited to the body motion sensor 5, and various components can be attached to the main unit 2, and such components can be attached to the fabric 50 through the fastener 1.

Moreover, according to this embodiment, although the description has been given of an example case in which the object to which the fastener 1 is attached is the clothing of the infant Hm, the fastener 1 can be attached to various objects like the fabric 50 with a certain thickness, such as the clothing of an adult and that of an aged person in addition to the infant Hm, the clothing of an animal, and the curtain of a room.

Eventually, the advantageous effects described in the present disclosure are merely examples and are not limited, and other advantageous effects may be accomplished, or only some of the advantageous effects described in the present disclosure may be accomplished. Moreover, the embodiments described in the present disclosure are merely examples, and the present disclosure is not limited to the foregoing embodiments. Hence, other than the foregoing embodiments, various changes can be made in accordance with designing, etc., without departing from the scope and spirit of the present disclosure. Note that the combination of all the structural components described in the embodiments is not always requisite to address the technical problem in some cases.

REFERENCE SIGNS LIST

1 Fastener
2 Main unit
3 Adjuster unit
4 Cover unit
5 Body motion sensor
24 Cylindrical protrusion
26 Bottom-surface opening
45 Circular opening
50 Fabric
Hm Infant

The invention claimed is:

1. A fastener comprising:
a main unit having a casing lid and a storage casing, the storage casing including a side wall, the side wall having a lower region and an upper region above the lower region in an up-down direction, the upper region of the side wall having an external side surface,
an adjuster unit which extends from the lower region of the side wall of the main unit, wherein the adjuster unit is capable of being elastically inflected; and
a cover unit coupled to the main unit through the adjuster unit,
wherein the cover unit is configured to be, by elastic flection of the adjuster unit, both in a state apart from the main unit and in a state latched with the main unit so as to cover the main unit, and
wherein with the cover unit being in the state latched with the main unit, the external side surface of the main unit and a surface of the adjuster unit are apart from each other, the surface of the adjuster unit is facing and opposed to the external side surface, and the surface of the adjuster unit overlaps the external side surface along the up-down direction.

2. The fastener according to claim 1, wherein the cover unit is latched with the main unit so as to cover equal to or smaller than a half of the main unit.

3. The fastener according to claim 1, wherein:
the main unit comprises a protrusion;
the cover unit is provided with an insertion opening; and
the protrusion is fitted in the insertion opening in the state in which the cover unit is latched with the main unit.

4. The fastener according to claim 1, wherein a body motion sensor that comprises one or a plurality of detecting units capable of detecting a body situation of a wearing person is attached to the main unit.

5. The fastener according to claim 4, wherein:
the detecting unit comprises at least an optical sensor to determine a contact state with a body of the wearing person; and
the optical sensor is placed so as to be exposed from an opening formed in the main unit.

6. The fastener according to claim 3, wherein the insertion opening forms a passage completely through the cover unit.

\* \* \* \* \*